United States Patent [19]

Foresta et al.

[11] Patent Number: 4,879,376
[45] Date of Patent: Nov. 7, 1989

[54] TRITERPENE SAPONINS HAVING ANTI-INFLAMMATORY, MUCOLYTIC AND ANTIEDEMIC ACTIVITIES, PROCESS FOR THE PREPARATION THEREOF AND PHARMACEUTICAL COMPOSITIONS CONTAINING THEM

[75] Inventors: Piero Foresta; Orlando Ghirardi, both of Rome; Bruno Gabetta; Aldo Cristoni, both of Milan, all of Italy

[73] Assignees: Sigma-Tau Industrie Farmaceutiche Riunite S.p.A., Rome; Inverni Della Beffa Industria Chimico Farmeceutica Derivati Naturali, Milan, both of Italy

[21] Appl. No.: 67,948

[22] Filed: Jun. 26, 1987

[30] Foreign Application Priority Data

Jul. 1, 1986 [IT] Italy ............................... 48208 A/86

[51] Int. Cl.$^4$ ................. A61K 31/705; A61K 31/70; A61K 35/78
[52] U.S. Cl. .................................. 536/18.1; 536/4.1; 536/5; 536/6.3; 536/128; 424/195.1; 514/26; 514/33; 514/34
[58] Field of Search ..................... 514/26, 33, 34; 536/4.1, 5, 4.4, 6.3, 18.1, 128; 424/195.1

[56] References Cited

U.S. PATENT DOCUMENTS

| | | |
|---|---|---|
| 3,886,272 | 5/1975 | Parkhurst et al. ............ 514/33 |
| 4,147,777 | 4/1979 | Mustich .......................... 514/33 |
| 4,524,067 | 6/1985 | Arichi et al. .................. 514/33 |

FOREIGN PATENT DOCUMENTS

| | | |
|---|---|---|
| 2543053 | 3/1977 | Fed. Rep. of Germany ........ 514/33 |
| 49-1711 | 1/1974 | Japan .............................. 536/18.1 |
| 2051575 | 1/1981 | United Kingdom ............... 514/33 |

OTHER PUBLICATIONS

Chirva et al.; Chemical Abstracts 81:120925z (1974).
Krokhmalyuk et al.; Chemical Abstracts 84:74569y (1976).
Higuchi et al.; Phytochemistry 26(1): 229-235 (1987).
Erdelmeier et al.; J. Chromatog. 389(1): 345-349 (1987).

Primary Examiner—Ronald W. Griffin
Assistant Examiner—Nancy S. Carson
Attorney, Agent, or Firm—Walter H. Schneider

[57] ABSTRACT

Triterpene saponins of formula

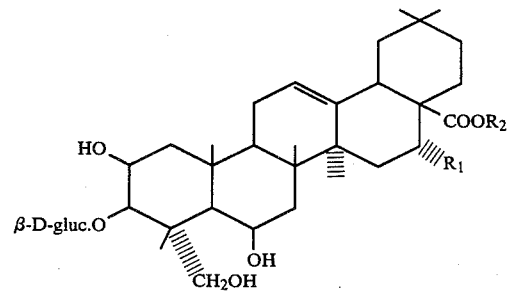

wherein $R_1$ is H or OH and $R_2$ is a tetrasaccharide, or alternatively pentasaccharide, chain have antiinflammatory, mucolytic and antiedemic activities. Said saponins are isolated from roots and bark of *Crossopteryx febrifuga*, for instance by precipitating them, in form of a complex with cholesterol or sytosterol, from an alcoholic extract of the vegetal material and by partitioning the precipitate between an apolar solvent, which subtracts the complexing agent and a polar solvent in which saponins are soluble.

8 Claims, No Drawings

TRITERPENE SAPONINS HAVING ANTI-INFLAMMATORY, MUCOLYTIC AND ANTIEDEMIC ACTIVITIES, PROCESS FOR THE PREPARATION THEREOF AND PHARMACEUTICAL COMPOSITIONS CONTAINING THEM

The present invention relates to two novel triterpene saponins, having antiinflammatory, mucolytic and antiedemic activity, of general formula

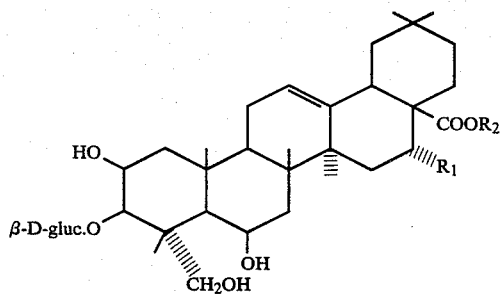

wherein:

$R_1$ is H or OH, and $R_2$ is a tetrasaccharide residue having 573 mass units or, alternatively, a pentasaccharide residue having 705 mass units, linked by means of an ester bond to the C-28 carboxyl.

For sake of shortness, the saponin wherein $R_1$ is H will be designated "Crossoptine A", whilst the saponin wherein $R_1$ is OH will be designated "Crossoptine B". The term "Crossoptine" is used since saponins of formula I may be isolated from roots and bark of *Crossopteryx febrifuga*, by means of a process which is another object of the present invention.

The present invention further relates to pharmaceutical compositions, particularly for topical administration, containing as the active ingredient one of the above cited Crossoptines, for the treatment of inflammatory and oedema conditions.

As it is clear from formula (I), Crossoptine A and Crossoptine B belong to the group of oleanolic acid saponins, and are characterized by the presence of alcohol residues at the $2\beta$, $3\beta$, $6\beta$ and 23 positions and, in the case of Crossoptine B, also at the $16\alpha$ position.

Crossoptines contain two saccharidic groups, consisting of a D-glucose residue, which is bound to the hydroxyl group at the 3-position and, as already mentioned, by a tetrasaccharide (573 mass units) or, alternatively, a pentasaccharide (705 mass units), connected to the C-28 carboxyl by an ester bond.

According to the structures of general formula I, mass spectrometry (FAB) revealed for Crossoptine A molecular weight of 1222 ($R_2$=tetrasaccharide); for Crossoptine B the HPLC analysis combined with mass spectrometry revealed the presence of two saponins in 1:1 ratio having molecular weight 1238 ($R_2$=tetrasaccharide) and 1370 ($R_2$=pentasaccharide).

*Crossopteryx febrifuga* is a plant with a shrub-type growth found all round the African tropical belt. The therapeutic activity of crude extracts from bark, roots and leaves of *Crossopteryx febriguga* is already known in african folk medicine, particularly the antipyretic activity—which gives the plant the name—, although the plant is known to have other various therapeutic applications. Depending on the areas and the traditions therein prevailing, antihelminthic activity, antidote activity against some poisons, and activity against chicken-pox, vertigo, syncope, stomach-ache, conjuntivitis or venereal diseases are attributed to *Crossopteryx febrifuga*.

The various source agree in considering *Crossopteryx febrifuga* active as an antipyretic agent.

These indications have been merely empiric, since no characterized product having a high and steady activity, or a reproducible process for its preparation were available, that could allow to verify its effective pharmacodynamic action from a rigorously quantitative point of view.

The isolation of the active principles on the other hand, allowed not only the possibility to carry out serious researches on its pharmacological effects, but also to detect its antiedemic analgesic and mucolytic activity, and the extraction of Crossoptine A and Crossoptine B from vegetal material may be carried out by means of alcohols having 1 to 3 carbon atoms, or aliphatic ketones and mixtures thereof with water. Hot-extraction of the drug with aqueous 80% methanol or ethanol is generally preferred.

The obtained extracts, after concentration under vacuum, are filtered to remove waxy materials, then they are subjected to counter-extraction with solvents having low polarity (hydrocarbons, chlorinated solvents, ethyl acetate, etc.) in order to remove the lipid components.

The purified aqueous solution may be then treated according to two alternative processes.

Accoding to a first process (process A) the solution is diluted with alcohols or water-miscible ketones to an about 50% concentration, and treated at ebullition with a 3-$\beta$-hydroxysterol excess (e.g. cholesterol or beta-sytosterol). Crossoptines A and B selectively form, with respect to the other extract components, insoluble complexes which are recovered by filtration and purified from any sterol excess by means of washing at room temperature with an hydrocarbon (e.g. n-heptane, toluene, etc.).

The complexes may be thereafter cleaved by partition between an apolar solvent (such as ethyl acetate or chloroform), which subtracts the complexing sterol, and a polar solvent (e.g. 50% aqueous methanol or acetone), in which Crossoptines A and B are soluble.

According to this procedure, a mixture of the two Crossoptines, substantially free from other extract components, may be obtained.

According to the second process (process B), the purified aqueous solution is extracted, together with other polar components, with water-immiscible alcohols (butyl alcohol, amyl alcohols, etc.). After concentration of the alcohol phase, a mixture of the two saponins having a sufficient purity grade is precipitated by dilution with apolar solvents (esters, chlorinated solvents, etc.).

The mixture of Crossoptine A and Crossoptine B, obtained by means of one of the above processes, may be finally separated into the two components by a chromatographic process on silica gel column, eluting with mixtures of chlorinated solvents, alcohols and water in appropriate ratios (for example chloroform-methanol-water in a 14:6:1 v/v ratio or in a 30:10:1 v/v ratio) or, where process A is used, also by simple fractional crystallization from isopropyl alcohol as such or in admixture with other alcohols.

The following non-limiting examples illustrate the extraction and isolation procedures for Crossoptines A and B.

EXAMPLE 1

Isolation of Crossoptine A and B in form of complexes with cholesterol (Process A)

2 kg of finely ground dry root of Crossopteryx febrifuga were extracted in a percolator with 6 l of 80% aqueous methanol for 5 times, under slight reflux. The combined percolates were filtered, then concentrated to 0.6 l under vacuum at a temperature not higher than 40° C.

The methanol concentrate was extracted 3 times with 0.6 l of n-hexane. The hexane phase, containing oily residues, was removed; the methanol phase, after distillation of hexane under vacuum, was diluted with methanol to 1 l, then with 1 l of water, and heated to 50° C. under strong stirring. 30 g of cholesterol were added portionwise to the mixture, keeping subsequently the suspension under stirring for 4 hours. The suspension was cooled and left to stand overnight at room temperature.

The complex of saponins with cholesterol was filtered and dried under vacuum for 24 hours, at a temperature of 60° C. 60 g of product were obtained, which was treated with 200 ml of toluene, left under stirring for 3 hours at room temperature, then filtered. After drying at 60° C. during a night, 32 g of product were obtained which, by HPLC analysis, proved to consist of 5 g of Crossoptine A and 15 g of Crossoptine B, complexed with 12 g total of cholesterol.

EXAMPLE 2

Isolation of Crossoptines A and B after cleavage of the complexes and column chromatography The mixture (32 g) of complexes obtained according to Example 1 was dissolved in 1.5 l of a chloroform-methanol 1:1 v/v mixture. The solution was added with 1 l of water; the phases were separated and the hydroalcoholic phase was counter-extracted with 0.5 l of chloroform in order to completely remove cholesterol.

The hydromethanolic solution, containing the saponins, was concentrated under vacuum to dryness, at a temperature not higher than 60° C. The residue (19 g) was chromatographed on a 1.2 kg silica gel column, previously balanced with a solvent mixture consisting of 70 parts of chloroform, 30 parts of methyl alcohol and 5 parts of water. The fractions homogeneous in thin layer chromatography were combined, concentrated under vacuum to dryness and the residues were crystallized from isopropanol. From the first fractions, 4 g of Crossoptine A were obtained, m.p. 221°–223° C. $[\alpha]_D^{25} -36.5°$ (c1, MeOH), M+ (FAB) m/z 1222, and 14 g of Crossoptine B, m.p. 218°–220° C., $[\alpha]_D^{25} -47.2°$ (c1, MeOH), The HPLC-MS analysis of Crossoptine 3 revealed the presence of two saponins in 1:1 ratio with M+1238 ($R_2$=tetrasaccharide) and M+1370 ($R_2$=pentasaccharide).

EXAMPLE 3

Isolation of Crossoptines A and B after cleavage of the complexes and fractional crytallization The mixture (64 g) of complexes obtained according to the procedure described in Example 1, cleaved into its components, according to the method disclosed in Example 2, gave 40 g of a mixture of A and B which was dissolved at ebullition in 500 ml of isoproyl alcohol and 200 ml of methyl alcohol.

Methyl alcohol was removed by concentration under vacuum and the mixture was left to crystallize overnight. The crystallized solid was filtered, washed with isopropanol and dried under vacuum at 60° C. to constant weight. 15 g of Crossoptine B were obtained having the same chemico-physical characteristics as above described.

Mother liquors from crystallization were concentrated under vacuum to incipient crystallization, then left to stand overnight.

The separated solid was filtrated, which consisted of 18 g of a mixture of Crossoptines A and B. From the mother liquors, by further diluton with 500 ml of ethyl ether, 5 g of crude Crossoptine A were precipitated, which was crystallized 3 times from isopropanol. 1.8 g of Crossoptine A were obtained, having the same chemico-physical characteristics as above reported.

EXAMPLE 4

Isolation of Crossoptines A and B by partition with solvents (Process B)

2 kg of finely ground roots of Crosopteryx febrifuga were extracted in percolator with 6 l of methanol 4 times, under slight reflux. The combined extracts were filtered and concentrated to syrup consistency.

The residue was taken up into 1.5 l of water; the aqueous solution was extracted 3 times with 0.5 l of ethyl acetate, saturated with water, and subsequently 3 times with 1 l of n-butanol containing 10% v/v of toluene.

The butanol extracts were concentrated under vacuum at a temperature not higher than 60° C. to 0.3 l. The butanol concentrate was poured into 1.5 l of isopropyl ether, in order to precipitate the saponins, which were filtered. After drying overnight at 60° C. under vacuum, 108 g of a residue were obtained, which was chromatographed on a column containing 1.5 kg of silica gel, previously balanced with a mixture consisting of 90 parts of $CHCl_3$; 30 of $CH_3OH$ and 3 of $H_2O$.

The fractions containing pure saponins were combined and concentrated to dryness under vacuum and the residues were crystallized 3 times from isopropyl alcohol.

3.5 g of Crossoptine A and 12 g of Crossoptine B were obtained, having the above reported chemico-physical characteristics.

PHARMACOLOGICAL TESTS (a) Acute toxicity ($LD_{50}$)

Crossoptine A showed a $LD_{50}$ by oral route of 350 mg/kg in the rat and Crossoptine B showed a $LD_{50}$ of 14 mg/kg by intraperitoneal route and 450 mg/kg by oral route, in the rat.

Crossoptines A and B proved to have antiinflammatory, antiedemic, analgesic and mucokynetic activities, in various pharmacological tests.

(b) Antioedema activity (carrageenin oedema test)

Antioedema activity was evaluated in the test of carrageenin oedema on rat paw, after oral and topical administration. The obtained results, in comparison with known active drugs, are reported in Table 1.

TABLE 1

Antiinflammatory activity of Crossoptine A and B in the carrageenin oedema in the rate

| Compound | Dose mg/kg os | No of animals | % inhibition in comparison with controls | | | | |
|---|---|---|---|---|---|---|---|
| | | | 1 hour | 2 hours | 3 hours | 4 hours | 5 hours |
| Crossoptine A | 100 | 10 | −85°° | −81°° | −81° | −70° | −53° |
| Crossoptine B | 100 | 10 | −88°° | −104°° | −93°° | −81°° | −58°° |
| ASA | 200 | 8 | −51°° | −39°° | −52°° | −45°° | −42°° |
| Phenylbutazone | 100 | 8 | −38° | −30° | −58°° | −54°° | −47°° |
| Escine | 50$^a$ | 10 | −39° | −44° | −51° | −49°° | −35° |

°°$p \leq 0.01$
°$p \leq 0.05$
$^a$maximal non-diarrhoic dose (c) Analgesic activity (phenylguinone writhing test)

Crossoptines A and B proved to have an analgesic activity, in the phenylquinone writhing, comparable to that of acetylsalicylic acid (ASA). (Table 2)

TABLE 2

Analgesic activity of Crossoptines A and B in phenylquinone writhing test in the mouse.

| Compound | Dose mg/kg os | No of animals | % Variation in comparison with controls |
|---|---|---|---|
| Crossoptine A | 50 | 10 | −31 |
| | 100 | 10 | −49 |
| Crossoptine B | 50 | 10 | −38°° |
| | 100 | 10 | −36° |
| ASA | 50 | 10 | −31°° |
| | 100 | 10 | −32°° |

°°$p \leq 0.01$ °$p \leq 0.05$ (d) Mucolytic activity

Crossoptine B, orally administered to the mouse in single and repeated doses, caused an increase in mucus excretion ranging from 48 to 70%. Comparison tests with control compounds (Bromhexine and Sobrerol) are reported also in Table 3.

TABLE 3

Expectorant activity of Crossoptine B in the mouse.

| Compound | Dose mg/kg | No of animals | % increase of sodium fluorescein excretion in comparison with controls |
|---|---|---|---|
| Crossoptine A | 50 × 1 | 6 | +47°° |
| Crossoptine B | 50 × 5 | 10 | +73°° |
| Bromhexin | 75 × 1 | 10 | +48°° |
| Sobrerol | 150 × 1 | 10 | +67°° |

°°$p \leq 0.01$ (e) DHT test (delayed-type hypersensitivity)

Male BDF$_1$ mice weighing 22-26 g were used in this delayed hypersentitivity test.

The procedure was the following:
0.2 ml of SRBC at a concentration of $5 \times 10^7$ cell/ml in phosphate buffer ($1 \times 10^7$ cell/mouse) (sensitizing injection) were administered subcutaneously in the front dorsal area of BDF$_1$ mice, divided into as many groups of 10 animals each as many were the administered doses of the compound under test, one group being the control.

The treated animals received the compounds dissolved in physiological saline, by intraperitoneal route, the day before, the same day and the day after the sensitizing injection. The control animals received, instead of the compound under test, the only solvent used to dissolve said compound.

4 days after the sensitizing injection, 50 ml of SRBC at a concentration of $2 \times 10^9$ cell/ml ($1 \times 10^8$) cell/mouse (challenge injection) were administered into the rear sx paw pad of the mice.

24 hours after the challenge injection the animals were killed by cerivical dislocation, rear paws were cut at the base and the differences in weight between sx paw (treated with the challenge injection) and the controlateral one were measured.

The weight differences between treated and controlateral control paws of each animals were evaluated, the obtained differences were valuated and standard error and significance of the results were calculated according to Dunnett's test.

TABLE 4

Effect of the compound administered by intraperitoneal route on the delayed hypersensitivity reaction in the mouse (DTH)

| Compound | Dose (mg/kg$^{-1}$) | Administration time with respect to hyper-sensitization (days) | Weight difference (mg ± E. S.) between treated and controlateral paws |
|---|---|---|---|
| Control | — | — | 51.75 ± 7.67 |
| Crossoptine A | 1 | −10 +1 | 42.37 ± 4.39 |
| Crossoptine A | 10 | −10 +1 | 19.42 ± 3.54$^\Delta$ |
| Control | — | — | 38.87 ± 2.68 |
| Crossoptine A (ripetition) | 10 | −10 +1 | 25.62 ± 3.37$^\Delta$ |
| Control | — | — | 40.20 ± 3.62 |
| Crossoptine B | 1 | −10 +1 | 32.80 ± 3.97 |
| Crossoptine B | 10 | −10 +1 | 23.40 ± 1.76$^\Delta$ |

$^\Delta$: $p \leq 0.01$ (Dunnett's test)

The above results prove that the novel triterpene saponins (I) are useful therapeutic agents, particularly antiinflammatory agents for the treatment of phlogosis of various etiology and mucolytic agents in the treatment of acute and chronic bronchitis having an inflammatory component.

Compounds (I) may be formulated in common pharmaceutical formulations, according to pharmaceutical techniques which are well known to the skilled in the art.

Some compositions according to the invention are reported hereinafter.

| Formulation of a ointment containing 1% of Crossoptine B | |
|---|---|
| Crossoptine B | 1 g |
| Excipients: | |
| Polyethylene glycol 2000 fatty acids esters | 2 g |
| Polysorbate 80 | 3 g |
| Cetyl alcohol | 10 g |
| Wheat germ oil | 2 g |
| Silicon oil 350 CPS | 0.5 g |
| Methyl and propyl p-oxybenzoate-mixture | 0.2 g |

| Formulation of a ointment containing 1% of Crossoptine B | |
|---|---|
| Butylhydroxyanisol | 0.05 g |
| Sodium ethylenediamino-tetraacetate | 0.02 g |
| Carboxyvinylpolymer (Carbopol 934) | 0.8 g |
| Triethanolamine | 1.2 g |
| Perfumed composition | 0.2 g |
| Depurated water | q. s. to 100 g |

| Formulation of 100 mg tablets containing 20 mg of Crossoptine B | |
|---|---|
| Crossoptine B | 20 mg |
| Excipients: | |
| Maize starch | 40 mg |
| Lactose | 26 mg |
| Polyvinylpyrrolidone | 5 mg |
| Silica powder | 3 mg |
| Carboxymethyl-starch | 3 mg |
| Magnesium stearate | 2 mg |
| Talc | 1 mg |

We claim:

1. A triterpene saponin of the general formula

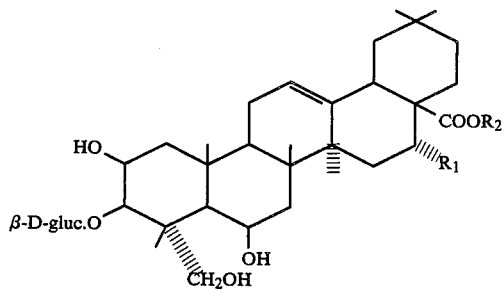

(I)

wherein:
$R_1$ is H or OH, and
$R_2$ is a tetrasaccharide residue having 573 mass units or a pentasaccharide residue having 705 mass units, wherein $R_2$ is attached to the C-28 carboxyl by an ester bond.

2. A triterpene saponin according to claim 1 in which $R_1$ is H.

3. A triterpene saponin according to claim 1 in which $R_1$ is OH.

4. A process for recovering a mixture of triterpene saponins of the formula according to claim 1 from an aqueous $C_{1-3}$ alcohol or an aliphatic ketone extract of the root and bark of *Crossopteryx febrifuga* which comprises: treating said aqueous extract at ebullition with a 3-beta-hydroxysterol to selectively precipitate a mixture of triterpene saponins as complexes with said 3-beta-hydroxysterol; separating and purifying said complexes; contacting said complexes with a mixture of an apolar solvent in which said 3-beta-hydroxysterol is selectively soluble and a polar solvent in which said mixture of triterpene saponins is selectively soluble; and recovering a solution of said mixture of triterpene saponins.

5. A process according to claim 4 in which said mixture of triterpene saponins is separated into its components by chromatographic analysis using an aqueous mixture of a chlorinated solvent and an alcohol as the eluant.

6. A process according to claim 4 in which said mixture of triterpene saponins is separated into its components by fractional crystallization with isopropanol alone or in admixture with other alcohols.

7. A process according to claim 4 in which said beta-hydroxysterol is selected from the group consisting of cholesterol and beta-sytosterol, said apolar solvent is selected from the group consisting of ethyl acetate and chloroform, and said polar solvent is selected from the group consisting of aqueous methanol or acetone.

8. A pharmaceutical composition having antiinflammatory, antiedemic, analgesic and mucolytic activities which comprises as the principal active ingredient a therapeutically effective amount of a triterpene saponin according to claim 1 in admixture with a pharmaceutically acceptable carrier.

* * * * *